US012693223B2

(12) United States Patent
Kalkbrenner

(10) Patent No.: US 12,693,223 B2
(45) Date of Patent: Jul. 28, 2026

(54) METHOD AND APPARATUS FOR DETECTING FLUORESCENCE SIGNALS IN A THREE-DIMENSIONAL REGION OF A SAMPLE

(71) Applicant: CARL ZEISS MICROSCOPY GMBH, Jena (DE)

(72) Inventor: Thomas Kalkbrenner, Jena (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 1144 days.

(21) Appl. No.: 17/309,510

(22) PCT Filed: Dec. 2, 2019

(86) PCT No.: PCT/EP2019/083219
§ 371 (c)(1),
(2) Date: Jun. 2, 2021

(87) PCT Pub. No.: WO2020/114930
PCT Pub. Date: Jun. 11, 2020

(65) Prior Publication Data
US 2022/0057329 A1 Feb. 24, 2022

(30) Foreign Application Priority Data

Dec. 3, 2018 (DE) ..................... 10 2018 220 779.8

(51) Int. Cl.
*G01N 21/64* (2006.01)
*G01N 33/542* (2006.01)
(Continued)

(52) U.S. Cl.
CPC ....... *G01N 21/6458* (2013.01); *G01N 33/542* (2013.01); *G02B 21/0076* (2013.01); *G02B 26/06* (2013.01); *G02B 27/0075* (2013.01)

(58) Field of Classification Search
None
See application file for complete search history.

(56) References Cited

U.S. PATENT DOCUMENTS

| | | | |
|---|---|---|---|
| 5,715,031 A | 2/1998 | Roffman et al. | |
| 7,009,651 B2 | 3/2006 | Ortyn et al. | |
| (Continued) | | | |

FOREIGN PATENT DOCUMENTS

| | | |
|---|---|---|
| DE | 69634282 T2 | 3/2005 |
| DE | 60218174 T2 | 3/2007 |
| (Continued) | | |

OTHER PUBLICATIONS

Fuller, et al., "Development of a robust immuno-S-FISH protocol using imaging flow cytometry : Immuno-S-FISH Analysis by Imaging Cytometry", NIH Public Access Author Manuscript, vol. 89, No. 8, May 8, 2016, pp. 720-730 (Year: 2016).*

(Continued)

*Primary Examiner* — Stuart D Bennett
(74) *Attorney, Agent, or Firm* — BRAKE HUGHES BELLERMANN LLP

(57) ABSTRACT

The disclosure relates to a detection method for optical signals in a three-dimensional region of a sample, and a detection method for marked antibodies and/or antigens on a biological surface. In the process, signals with a depth of field that is extended in relation to an original depth of field are captured and evaluated. Also, an apparatus includes an optical element in a detection beam path, a depth of field that is extended in relation to an original depth of field being generated by the effect of said optical element.

13 Claims, 14 Drawing Sheets

(51) Int. Cl.

| | | |
|---|---|---|
| *G02B 21/00* | (2006.01) | |
| *G02B 26/06* | (2006.01) | |
| *G02B 27/00* | (2006.01) | |

(56) References Cited

U.S. PATENT DOCUMENTS

| | | | |
|---|---|---|---|
| 7,161,656 | B2 | 1/2007 | Neil et al. |
| 8,005,314 | B2 * | 8/2011 | Ortyn ................. G02B 27/0075 |
| | | | 359/30 |
| 8,908,174 | B2 | 12/2014 | Kempe et al. |
| 8,988,771 | B2 | 3/2015 | Kleppe et al. |
| 9,176,152 | B2 | 11/2015 | Knutson et al. |
| 9,201,011 | B2 | 12/2015 | Kalkbrenner et al. |
| 9,582,927 | B2 | 2/2017 | Bublitz et al. |
| 9,690,882 | B2 | 6/2017 | Dobschal |
| 10,031,325 | B2 | 7/2018 | Anhut et al. |
| 10,042,153 | B2 | 8/2018 | Kalkbrenner |
| 10,234,667 | B2 | 3/2019 | Novikau et al. |
| 2010/0278400 | A1 | 11/2010 | Piestun et al. |
| 2011/0174986 | A1 * | 7/2011 | Kempe ................. G02B 21/16 |
| | | | 250/216 |
| 2011/0249866 | A1 | 10/2011 | Piestun et al. |
| 2015/0043060 | A1 | 2/2015 | Huber et al. |
| 2015/0053872 | A1 * | 2/2015 | Kjaerulff ............ G02B 27/0961 |
| | | | 250/206 |
| 2017/0068080 | A1 * | 3/2017 | Anhut ................. G02B 21/365 |
| 2017/0205609 | A1 * | 7/2017 | Fukuyama ......... G01N 21/6458 |
| 2018/0149855 | A1 | 5/2018 | Chou et al. |

FOREIGN PATENT DOCUMENTS

| | | |
|---|---|---|
| DE | 102008049886 A1 | 4/2010 |
| DE | 102010013223 A1 | 9/2011 |
| DE | 102010044013 A1 | 5/2012 |
| DE | 102011114752 A1 | 4/2013 |
| DE | 102012207003 A1 | 10/2013 |
| DE | 102012212801 A1 | 1/2014 |
| DE | 102013208415 A1 | 11/2014 |
| DE | 102014102215 A1 | 8/2015 |
| DE | 102015107367 A1 | 11/2016 |
| DE | 102016116620 B3 | 11/2017 |
| DE | 102016219632 A1 | 4/2018 |
| DE | 102018217115 A1 | 11/2018 |
| JP | H04171415 A | 6/1992 |
| JP | H1062694 A | 3/1998 |
| JP | 2000318248 A | 11/2000 |
| JP | 2015516063 A | 6/2015 |
| JP | 2017507361 A | 3/2017 |
| WO | 2010045949 A2 | 4/2010 |
| WO | 2015189240 A1 | 12/2015 |
| WO | 2016152244 A1 | 9/2016 |

OTHER PUBLICATIONS

English Translation of International Search Report for PCT/EP2019/ 083219, Feb. 26, 2020, 3 pages.

International Preliminary Report on Patentability for PCT Application No. PCT/EP2019/083219, mailed on Jun. 17, 2021, 12 pages.

Fuller, et al., "Development of a robust immuno-S-FISH protocol using imaging flow cytometry : Immuno-S-FISH Analysis by Imaging Cytometry", NIH Public Access Author Manuscript, vol. 89, No. 8, May 8, 2016, pp. 720-730.

Mizoguchi, et al., "High-speed variable-focus optical system for extended depth of field", Industrial Electronics, 2009. ISIE 2009. IEEE International Symposium on, IEEE, XP031519237, Jul. 5, 2009, pp. 1668-1673.

Ortyn, et al., "Extended depth of field imaging for high speed cell analysis", NIH Public Access Author Manuscript, vol. 71A, No. 4, Jul. 5, 2007, pp. 215-231.

Pavani, et al., "Thee-Dimensional, Single-Molecule Fluorescence Imaging Beyond the Diffraction Limit by Using a Double-Helix Point Spread Function", PNAS, vol. 106, No. 9;, Mar. 3, 2009, 6 pages.

Pavani, et al., "Three Dimensional Tracking of Fluorescent Microparticles Using a Photon-Limited Double-Helix Response System", Optics Express, vol. 16, No. 26, Dec. 22, 2008, 10 pages.

Quirin, et al., "Optimal 3D Single-Molecule Localization for Super-resolution Microscopy With Aberrations and Engineered Point Spread Functions", PNAS, vol. 109, No. 3;, Jan. 17, 2012, pp. 675-679.

Zalevsky, et al., "Extended depth of foc us imaging with birefringent plat", Optics Express, vol. 15, No. 12, XP055669009, Jun. 11, 2007, pp. 7202-7210.

* cited by examiner

METHOD AND APPARATUS FOR DETECTING FLUORESCENCE SIGNALS IN A THREE-DIMENSIONAL REGION OF A SAMPLE

CROSS REFERENCE TO RELATED APPLICATION

This application is a 35 U.S.C. § 371 National Phase Entry Application from PCT/EP2019/083219, filed Dec. 2, 2019, designating the U.S., and claims the benefit of German Application No. 10 2018 220 779.8, filed Dec. 2, 2018, the disclosures of which are incorporated herein by reference in their entireties.

TECHNICAL FIELD

The invention relates to a detection method for light signals, in particular, in the case of a biological sample.

BACKGROUND

The prior art has disclosed a number of super-resolution methods, by means of which induced light signals of biological samples can be captured and evaluated. In this context, super-resolution microscopy methods such as, e.g., PALM (photoactivated localization microscopy), STORM (stochastic optical reconstruction microscopy), or dSTORM (direct stochastic optical reconstruction microscopy), in particular, are mentioned.

In the aforementioned methods, individual molecules provided with a switchable fluorescence marker (fluorophores) are localized by virtue of these fluorescence markers (which are also abbreviated as markers below) being successively activated and/or excited. The excited markers emit a fluorescence radiation that can be captured, and the position of the relevant marker can be localized. The sequential or successive activation and/or excitation of individual markers can also be considered to be an isolation process, in which fluorescence signals of individual molecules can be captured, even if their location relative to one another is below the resolution limit.

Isolation and localization with the aid of the PALM or dSTORM method (e.g., single molecule localization microscopy), for example, is described in, e.g., U.S. Pat. No. 8,988,771 B2. In this case, the use of photoswitchable markers allows the successive activation/excitation and subsequent localization of subsets of the markers, which are coupled to antibodies, for example. Hence, the fluorophores, and thus also the antibodies, can be quantified with a sensitivity on the level of individual molecules.

A disadvantage of the specified methods of the prior art is that the samples usually have a 3-D structure and, in general, a requirement of this 3-D structure is that as a whole it can be captured only by a focus stack. To this end, a multiplicity of individual images have to be recorded for each plane of the focus stack in order to be able to capture the molecules to be quantified with the desired accuracy. Moreover, the photoswitchable markers can only be captured in the focal plane or in the depth of focus of the microscope objective. However, the markers are present in three dimensions within the biological samples and portions thereof are also activated and/or bleached above and below the current focal plane. By way of example, prematurely bleached markers are no longer captured once the data capture is implemented in the focal plane in which the relevant marker is in fact present.

This disadvantageous effect is elucidated in FIG. 1. In a microscope 1 that is only indicated here, illumination radiation is directed along an illumination beam path 2 not illustrated in any more detail (see FIGS. 3 to 8), through a slide 6 and at the sample 7 by means of an objective 5. The sample 7 is a cell that has been modified with photoswitchable markers 8. By way of example, the markers 8 are bound to antigens 9 (not shown), which are located at the cell membrane of the sample 7.

The focal plane respectively set by means of the objective 5 has a small extent in the direction of the Z-axis on account of optical and technical boundary conditions, which is also referred to as DOF (depth of focus) and elucidated in exemplary fashion by a double-headed arrow. Nominally, this focal plane corresponds to the depth of field of the objective 5.

At a capture time, the excited markers 8 emitting fluorescence radiation as detection radiation, which are present in the respective focal plane DOF, are captured as signals 12 by means of the detector 13, for example, a camera, by way of the objective 5. In this case, further optical elements such as, e.g., a tube lens 10 can be present in the detection beam path 3.

It is evident from schematic FIG. 1 that only the two markers 8 situated within the focal plane DOF are captured by the detector 13 at the illustrated time. In order to obtain an image of the entire sample 7, the former must be generated from an image stuck. The image stack is obtained by virtue of the focal plane DOF being displaced in the direction of the Z-axis (Z-direction) by a displacement of the objective 5 (of the slide 6, not shown), for example, and respective images being captured at suitable pitches of the focal planes DOF. The different focal planes DOF and positions of the objective 5 are symbolized by horizontal dashed lines. The point spread function PSF in the direction of the Z-axis Z is illustrated schematically.

It is very important for some applications of photoswitchable markers that no marker escapes detection. Such false negative results, in which markers actually present are not detected, are very disadvantageous, for example, when researching antigens on cells and/or when detecting antibody-antigen bindings.

SUMMARY

Techniques described herein are based on the object of proposing an option for ascertaining a number of fluorescence signals in a three-dimensional region of a sample, by means of which the disadvantages of the prior art are reduced.

The object can be achieved by detection methods and an apparatus according for carrying out the methods as disclosed in the claims.

The detection method for fluorescence signals in a three-dimensional region of a sample includes capturing image data in the three-dimensional region by means of an optical apparatus, with the image data being imaged and captured in a two-dimensional image plane. The number of fluorescence signals in the image plane is ascertained, assigned to the region of the sample, and stored. The numbers, thus assigned and stored, are provided for retrieval.

According to an implementation, the fluorescence signals are captured by virtue of the extent of a focal plane being increased in the direction of the optical axis of the optical apparatus, in particular, in the direction of a detection axis of the optical apparatus, and a focal region being formed. The fluorescence signals captured in the three-dimensional region by means of this EDOF (extended depth of focus) approach are projected into the image plane and captured as a two-dimensional image representation.

Within the meaning of this description, a focal plane is the nominal depth of field of the utilized objective. An increased depth of field can be composed of a plurality of focal planes or a plurality of focal regions, wherein a focal region represents a depth of field that is extended in relation to the original depth of field of the objective.

The concept consists of implementing the 2-D projection of all fluorescence events, i.e., all fluorescence signals, from a given 3-D volume of the sample, e.g., a cell, onto at least one detector. To this end, the volume to be imaged is captured in the Z-direction by means of a suitable EDOF optical unit. It has been recognized that a significant improvement in the quantitative detection accuracy is achieved if the advantage of the three-dimensional resolution of the captured image data and fluorescence signals is dispensed with. In this way, technical improvement is achieved in one field, counting signals, by virtue of measures being taken in another field, capturing in super-resolution.

The information about the position of a fluorescence signal-emitting marker along the Z-axis (Z-direction, detection axis) can be deliberately relinquished in this case. The precision in the lateral localization can also be reduced since the object of the method according to the invention is not that of structural super-resolution. Thus, a highly sensitive count of fluorescence signals can be achieved. Naturally, additionally arising super-resolved 2-D spatial information can be used, for example, to examine antibody distributions on cell membranes more accurately.

The capture of fluorescence signals using the EDOF approach or EDOF method described herein can be distinguished from known representation methods, for example, the maximum intensity projection (MIP). Both positive and negative image values can be captured and imaged by means of the EDOF method. Thus, negative image values (pixel values) may occur in the case of phase gradient methods, MIP being unsuitable for the capture thereof, but EDOF allows high-quality image data to be captured (in this respect, see, e.g., Giese et al. (2014): Fast volumetric phase-gradient imaging in thick samples; Optics Express 22: 1152-1162, which is incorporated herein by reference).

In a further implementation, it is possible to detect antigens on biological surfaces with detection methods disclosed herein. The detection methods include incubating the biological surface with at least one antibody, which binds to the antigen to be detected and which is provided with a marker. The markers suitable for the emission of light signals, for example, for the emission of excited fluorescence radiation, and hence for the emission of fluorescence signals. Alternatively, use is made of a biological surface that has been incubated with such a marked antibody. The antibodies preferably bound to an antigen are excited to emit light signals, in particular fluorescence signals. This can be brought about by excitation radiation, for example. Image data that can comprise emitted light signals are captured by means of an optical wide field arrangement and an EDOF optical unit. The structure of an advantageously used wide field arrangement is explained in detail below.

Antigens are understood to mean compounds or molecules, for example, proteins, carbohydrates, lipids, DNA molecules, saccharides, and heavy metals, which can specifically bind the antibodies. Specific binding is implemented at epitopes of the antigens, wherein an antigen can have a plurality of epitopes.

The captured image data are evaluated in respect of the presence of captured fluorescence signals and a number of the captured light signals is ascertained, stored, and provided.

Photoswitchable molecules can be used as markers in one configuration of the method. During the capture of the fluorescence signals, a subset of the number of markers is excited to emit light signals (fluorescence signals) during each period of time. The emitted light signals are captured in a time series. Using such a configuration of the method, the number of those markers which are located very close together in space or which lie in succession in the direction of the Z-axis and which would otherwise be imaged in a common point of the image plane is also able to be captured. The markers are isolated in view of the detection by the capture in a time series.

The specific procedure that is carried out during the isolation and during the localization of the origin of the respective fluorescence signal depends on the utilized marker or the utilized markers. In the process, the point spread function (PSF), which is modified by the EDOF method, is considered and taken into account during the evaluation of the image data.

The markers utilized can be dyes within the meaning of WO 2006/127 692 A2 (PTOL, phototransformable optical labels). Examples of this are photoconvertible or photoswitchable fluorescent proteins such Dronpa, EOS, etc., and the derivatives thereof. It is also possible to use synthetic dyes such as Alexa 647 as markers, which can be brought into long-lived dark states by light and/or (chemical) modification of the ambient conditions. Moreover, the use of caged dyes, such as caged rhodamine is possible (Grimm, Jonathan B., et al.; 2013: Carbofluoresceins and carborhodamines as scaffolds for high-contrast fluorogenic probes; ACS chemical biology; 8.6: 1303-1310).

The detection methods disclosed herein can be used to detect a plurality of different markers or a plurality of antigens provided with different markers.

In further configurations of the methods, the extended depth of field and/or further optical parameters can be adapted on the basis of the respective sample. In one possible configuration, it is possible for the extended depth of field to be set itself. As an alternative or in addition thereto, it is possible to produce at least two focal planes. If at least two of the focal planes intersect or adjoin one another, it is possible to generate at least one focal range with an extended depth of field in this way, too. Within the meaning of this description, there is also an extended depth of field if two or more focal regions are generated, which do not intersect in the direction of the detection axis (Z-direction) but overall image a larger region in focus than the original depth of field in the direction of the detection axis.

As a result, it is possible to generate an extended depth of field by virtue of at least two focal planes with an original depth of field or at least two focal regions with an extended depth of field or at least one focal plane with an original depth of field and at least one focal range with an extended depth of field being generated.

Such imaging, which is also referred to as bifocal or multifocal, can be set in such a way that, for example, only a lower and an upper cell membrane of the sample are captured at the same time by means of bifocal imaging. An advantage in this case lies in a reduction of the image data to the regions of the sample that are of interest (region of interest; ROI). Moreover, fluorescence photons are used more efficiently. By way of example, the entire volume of the sample can be captured by means of multifocal imaging.

An independent evaluation of the individual focal planes or focal regions is possible at a later stage.

In method configurations in which an overlap of all or at least some of the focal planes/regions is sought after by means of multifocal imaging with EDOF, it is necessary to avoid fluorescence signals (signals) being captured twice. By way of example, this can be implemented by virtue of the captured signals on the different regions of the detector being compared to one another. If the signal of a marker or a marked antibody is captured in different regions of the detector, it is only counted once. By way of example, such two-time capture of the same signal can be verified by means of a comparison and evaluation of the spatial coordinates in the detector regions. It is also possible to carry out a correlation of the captured signals of the picture elements or pixels of the detector prior to an evaluation.

In further configurations of the method, the sample can be illuminated using a light sheet. The latter can be produced with a thickness corresponding to an EDOF region.

Even though information about a Z-position of a location of origin of a captured signal is relinquished either completely or, in the case of multifocal imaging, largely by the use of configurations of the detection methods disclosed herein, two-dimensional localization can continue to be implemented. Such 2-D localization of the fluorescence signals is undertaken on the basis of the respectively selected EDOF method and the PSF arising therefrom. In this case, it is possible, for example, to carry out localization by determining the centroid of the PSF and by using a theoretical PSF or an experimentally determined PSF. Moreover, is possible to carry out a localization by fitting analytical functions or approximations, e.g., a 2-D Gaussian function. In a further configuration of the method, the EDOF function can be generated using an axicon. In such a case, it is possible to choose a Bessel function which, as a result, leads to a Bessel PSF.

The localization step is preceded by the recognition of the fluorescence signals, in particular in the form of "spots" in the detector frame (raw data). To this end, thresholds of the ratio of captured intensity to captured background are usually set. Captured intensities (intensity peaks), which exceed these thresholds by at least one pixel, are assigned to the relevant pixel with a fixed radius. By way of example, such a radius can be defined as 2.5*PSF width at the FWHM (full width at half maximum). The data of pixel and radius are then incorporated in the localization step.

When carrying out the method, the radius can be chosen to be larger since the PSF, despite EDOF, may have a dependence on the Z-direction and may become larger in this direction. Alternatively, the radius can also be adapted for each intensity peak, for example, by virtue of the radial drop of intensity in the detector plane being analyzed over the neighboring pixels.

Should an isolation of markers or marked antigens not be possible or not be possible with a sufficient quality, a multi-emitter algorithm can be used for localization, as described in, e.g., Holden et al., 2011 (Holden, S. J.; Uphoff, S., and Kapanidis, A. N., (2011): "DAOSTORM: an algorithm for high-density super-resolution microscopy." Nature methods 8.4: 279).

It is furthermore possible to carry out a cluster analysis with the localization data in order to assign multiple localizations of a marker or multiply marked antibodies to one target molecule (antigen). Ultimately, the object of such an assignment is the ascertainment of the number of antibodies per cell.

Implementations can be supplemented by virtue of the perimeter of the cell, for example, being ascertained using a non-fluorescing contrasting method. Parameters of the cell such as its perimeter can be used as reference value, in respect of which it is possible, for example, to specify the ascertained number of markers or antigens. By way of example, in addition to the total number of markers ascertained, it is also possible to ascertain, store, and/or output the number of markers per unit length of the cell perimeter. To this end, it is possible to determine for example the extent and/or contour of a cell. Non-fluorescing contrasting methods include, for example, DIC (differential interference contrast), transmitted light contrast, phase contrast or the use of angular illumination microscopy.

To obtain reproducible results and, in particular, to assist the isolation of the markers, the densities of the emitters, i.e., the markers or the marked antigens, can be set taking account of the chosen projection and the utilized PSF in advantageous configurations. For evaluation and localization, it is possible to undertake a deconvolution on the basis of a system PSF. The term system PSF, in particular, is understood to mean a measured PSF which, in contrast to theoretical PSF, contains the actual properties of the optical system (aberrations, etc.). Thus, the system PSF corresponds to the EDOF PSF of the optical system.

The object is further achieved using an apparatus for detecting fluorescence signals or induced light signals in a three-dimensional region of a sample. The apparatus has a detection beam path. Detection radiation present is guided along the detection beam path and can be captured using suitable means such as a detector.

An objective with an original depth of field in the direction of a detection axis is present in the detection beam path for the purpose of capturing the detection radiation. The detection axis extends along the detection beam path, at least between objective and sample. In this description, the original depth of field is understood to be the nominal depth of field of the objective, as would be present and usable without the EDOF approach described below.

Implementations an include an optical element in the detection beam path, with the optical element having such optical power that a depth of field that is extended in relation to the original depth of field is generated by means of the optical element. This extension of the depth of field is obtained by lengthening the focus (focal lengthening) in the direction of the detection axis. The optical element is preferably arranged in a pupil of the detection beam path. Possible advantageous embodiments of the optical element are explained further below.

The apparatus includes a detector for capturing image data of individual fluorescence events/signals, where the capture of the fluorescence signals (also signals for short) is implemented or can be implemented in two-dimensional fashion and/or in temporally resolved fashion. Moreover, an evaluation unit is present, in which the image data read from the detector are evaluated and a number of the fluorescence signals is ascertained, assigned to an image region, and stored.

The apparatus that can be used for carrying out the detection methods can orient itself substantially to a microscope design for fluorescence wide field microscopy with laser-based excitation, as is known from the PALM, STORM and dSTORM methods, for example. The additional EDOF function is realized in the detection beam path.

The optical element can be a phase mask in one possible configuration. A phase mask can be static and produced by lithography, for example. In further embodiments of the apparatus, it can be dynamic and be realized by spatial light modulators (SLMs), this being possible either in transmission or in reflection. A static phase mask advantageously reduces the required control steps while a dynamic phase mask advantageously gives the apparatus greater flexibility.

In further embodiments, an axicon or an axicon phase mask can be arranged in the detection beam path as an optical element. The detection radiation is converted into a Bessel beam by the action of such an optical element.

In terms of the present problem, the advantage of the Bessel beam lies in its great depth of field, a simple generation, a defined Bessel PSF, and a large EDOF range. Its extended ring system is disadvantageous since much energy or many of the fluorescence photons enter into this ring system and are therefore not available, or are only available to a restricted extent, for localization. By way of example, a ring phase mask can be used as phase mask. The phase mask can optionally be subject to so-called phase wrapping and hence, for example, be realized by a spatial light modulator. Phase wrapping is understood to mean the generation of a phase distribution which, for example, needs to be generated by means of the spatial light modulator in order, as a result, to bring about a desired phase distribution. Since, as a rule, a spatial light modulator can realize a phase angle deviation from 0 to $2\pi$ (2 pi), a number of local phase angle deviations up to $2\pi$ are generated for producing large phase angle deviations of $N*2\pi$. As a consequence of destructive and constructive superpositions of the beams modulated by means of the spatial light modulator, a desired phase distribution with phase angle deviations of, e.g., $N*2\pi$ are set as a result. In this way, it is possible to realize, for example, an axicon with a phase angle deviation of $N*2\pi$ as a phase function.

A cubic phase mask is arranged in the detection beam path as an optical element in a further embodiment of the apparatus. Said phase mask can be embodied symmetrically or asymmetrically.

Phase masks such as the mentioned cubic phase mask, the axicon or the ring phase mask described below are arranged in a Fourier plane (=pupil) or in the vicinity thereof. To this end, the phase mask can be arranged either in the objective pupil or in a further pupil accessible by way of an intermediate image. The latter is advantageous in that the excitation radiation is not influenced by the phase mask.

If the optical element is realized by a ring phase mask, so-called phase rings can be brought about as optical effects. If the phase rings are binary and if these have a phase shift of $\pi/2$ between the phase rings, the resultant point spread function (PSF) has two maxima. By way of example, such a phase mask and PSF can be used for a targeted capture of, e.g., upper and lower cell membrane or other different regions of the sample.

The manifestation of the maxima can be influenced by further ring elements. By way of example, phase angles between 0 and $\pi/2$ can lead to a reduction in the bifocal character.

The concept of bifocal imaging and the use of an extended depth of field accompanied thereby can be achieved in further embodiments of the apparatus by virtue of a birefringent element being arranged in the detection beam path as an optical element.

The principle of operation of such a birefringent element in the detection beam path makes use of the circumstance that the signals of the markers have isotropic polarization on average. The birefringent element has different refractive indices, and hence different optical path lengths, for orthogonal polarizations. Hence, this results in bifocal imaging for the isotropically polarized fluorescence radiation. The two focal regions can also merge into one another and thus form a contiguous EDOF region. In a further embodiment, the birefringent element does not take over the entire cross section of the beam path. By way of example, a third image plane arises in such a case, i.e., a third focal region within the meaning of a third depth of field is generated along the detection axis.

As an alternative to the analytically representable phase masks presented above, phase masks can also be ascertained and represented iteratively by algorithm. To this end, it is possible, for example, to define a quality function which describes the desired EDOF properties of the PSF, such as, e.g., length of the PSF, width (x/y) at different z-positions. Subsequently, a start phase function is specified, the latter being altered iteratively and the alterations only being adopted if the quality function increases. In this way, it is possible to iteratively maximize the quality function. The iterative alteration can be implemented stochastically ("random walk").

Likewise, it is possible to use a so-called IFTA (inverse Fourier transform algorithm) (Gerchberg-Saxton-Algorithmus; Gerchberg, R W and Saxton (1972): A practical algorithm for the determination of the phase from image and diffraction plane pictures; Optik 35: 237-46). The latter needs to be extended to 3-D in the present case (e.g., Whyte, G. and Courtial, J. (2005): Experimental demonstration of holographic three-dimensional light shaping using a Gerchberg-Saxton algorithm; New Journal of Physics 7.1: 117). Here, too, a target function is specified, the desired EDOF-PSF intensity distribution in this case, and the latter is then iteratively approximated by the IFTA algorithm.

Using such iterative algorithms, it is possible to suitably set the target EDOF behavior and the resultant phase mask for the optical system present can then be manufactured.

If a variable, phase-shaping element such as an SLM (spatial light modulator) or else a deformable mirror is provided for the optical system, the aforementioned iterative optimizations can also be carried out between individual experiments, e.g., for different sample classes.

The apparatus can include at least one adaptive optical element in the detection beam path in a further embodiment. Such optical elements are, in particular, a variable lens, an adaptive, more particularly deformable, mirror or a micro-lens array. The adaptive mirrors are used in reflection.

By way of example, if a liquid lens is used as a variable lens for the dynamic EDOF approach, the latter can be positioned, for example, in the infinity space of an intermediate image. Variable lenses are often configured in such a way that they have no refractive power or only a very low refractive power in an un-driven state. Therefore, a static correction lens can optionally be present.

A so-called dynamic EDOF method is implementable by means of such an embodiment with an adaptive optical element. In this case, a quick focal displacement can be brought about, with such a focal displacement being implemented within a capture time interval of the detector, for example, within a camera exposure time. Moreover, the functionality of the EDOF method can be flexibly adapted to the sample. By way of example, the extended depth of field can be matched to a mean extent of the cells to be examined in the direction of the detection axis (Z-direction).

If the morphology of the sample to be examined is known, the focal displacement can also be implemented in targeted fashion, e.g., to the upper and the lower cell membrane, instead of continuously running through the entire volume. By way of example, the lower cell membrane is the first cell membrane virtually intersected by the detection axis when coming from the objective. Accordingly, the upper cell membrane which is intersected second and situated further away from the objective. A selective selection and adjustment of the focal positions increases the photon efficiency since no integration time of the detector is used at sample positions that are not of interest.

The respective positions of the cell membranes of a sample can vary in the direction of the detection axis. Therefore, it is advantageous if bifocal or multifocal imaging is combined with a further EDOF method or optionally is combinable with the latter. A two-stage effect is achieved in this way: two regions of the sample that are to be imaged are coarsely predefined (e.g., upper and lower cell membrane) by way of the bifocal or multifocal imaging of the detection radiation. Then, all molecules within the respective coarse region are captured by means of the additional EDOF method (e.g., using a cubic phase mask as an optical element). In this case, the two coarse regions can advantageously be imaged on dedicated detector regions or detectors.

By way of example, splitting the detection radiation coming from a plurality of focal planes or focal regions can be implemented by means of a suitable image splitter device, due to the effect of which a plurality of image planes or focal regions are simultaneously imaged on correspondingly many portions of a detector and/or on a plurality of detectors. Examples of such image splitter devices are arrangements with a second detector with a slightly different spacing in relation to a first detector (e.g., Ram, Sripad, et al., 2008: High accuracy 3D quantum dot tracking with multifocal plane microscopy for the study of fast intracellular dynamics in live cells.; Biophysical Journal 95: 6025-6043), a variable plane setting on a plurality of detector regions (DE 10 2009 060 490 A1), a diffractive element for aberration-corrected imaging of a plurality of focal planes on a plurality of detector regions (WO 2013/106731 A1), or prism arrangements for imaging a plurality of focal planes on portions of a plurality of detectors (WO 2015/044819 A1).

An advantage of the methods and apparatus described herein lies in the option of an improved accuracy when ascertaining the number of markers and/or marked antigens. By means of the suitable EDOF phase element arranged in a pupil, it is possible, in particular if the splitter arrangement and/or phase element has a variable design, to adapt counting of molecules in a 3-D sample to the extent in the Z-direction of the sample without needing to capture a focus stack. By way of example, if a variable multifocal apparatus is used, the focal planes in the case of adherent cells can be set in such a way that these respectively capture the upper and the lower cell membrane. Around the focal planes, the (additional) EDOF element brings about the corresponding extension of the depth of field and consequently brings about appropriate focal regions. In an advantageous implementation, the optical element causes the two focal regions to slightly overlap. In this way it is possible to capture the entire cell. When the techniques described herein are applied to samples which have a significantly greater extent in the z-direction than cells, e.g., suspension cells, and if the distance cannot be bridged with the aid of the optical element either, it is optionally also possible to capture more than two focal regions simultaneously.

The apparatus can be advantageously used to ascertain a number of signals, in particular fluorescence signals, of a biological cell, of a region of a biological cell, or of a biological structure. Moreover, it can be used in a method for detecting fluorescence-marked biological cells, biological structures, and for detecting marked antibodies and bindings of marked antibodies to antigens.

BRIEF DESCRIPTION OF THE DRAWINGS

The invention is explained in more detail below on the basis of exemplary embodiments and figures. In the drawings.

DETAILED DESCRIPTION

Implementations disclosed herein are illustrated schematically. Here, the same reference signs denote the same technical elements in each case.

Figure 2:
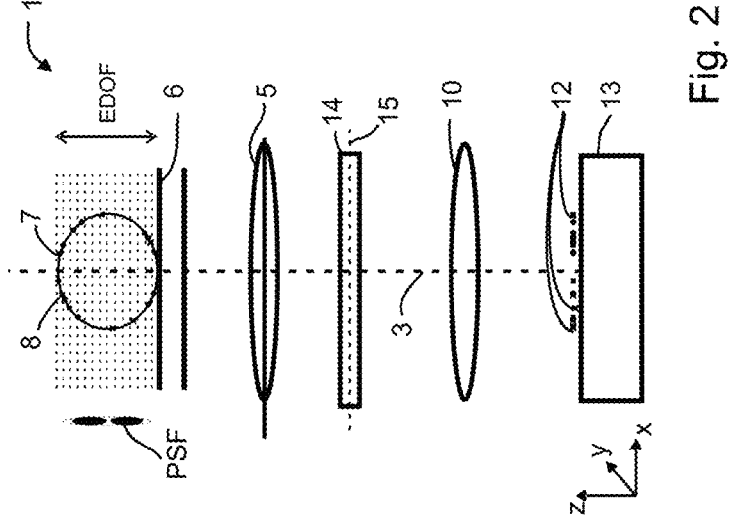
FIG. 2 shows a schematic illustration of a detection method by means of a first exemplary embodiment of an optical apparatus and a focal region corresponding to an extended depth of field of an objective.
Figure 1:
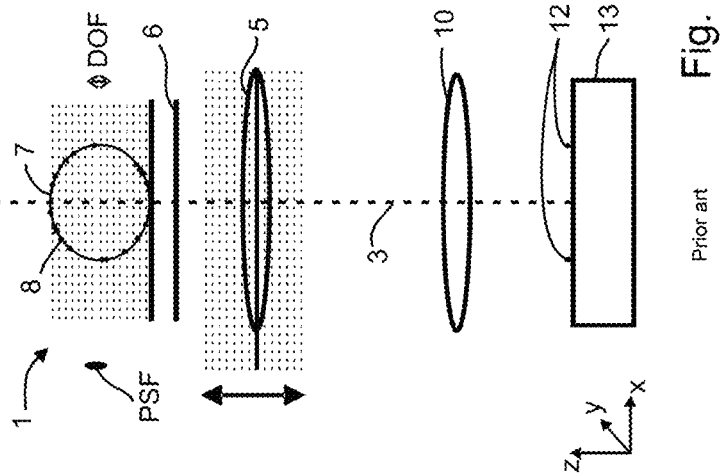
FIG. 1 shows a schematic illustration of a detection method by means of an optical apparatus and a focal plane corresponding to an original depth of field of an objective in accordance with the prior art.

An example implementation is illustrated in FIG. 2 and is compared to the prior art illustrated in FIG. 1. An optical element 14, the effect of which leads to the depth of field of the objective 5 being extended, is arranged in the detection beam path 3 of an optical apparatus. The point spread function PSF is extended in the direction of the Z-axis Z. This extended depth of field EDOF (elucidated by a double-headed arrow) facilitates the capture of the entire sample 7 in the direction of the Z-axis Z with only a single focus setting of the objective 5 in this exemplary embodiment. Accordingly, all markers 8 bound to the sample 7 can be imaged simultaneously by capturing their respective (fluorescence) signals 12 by means of the detector 13. The information about the position of the location of origin (marker 8) of a respectively captured signal 12 in the direction of the Z-axis Z is lost in the process. A marker 8 can only be localized in the detection plane along the X and Y axes.

Figure 3:
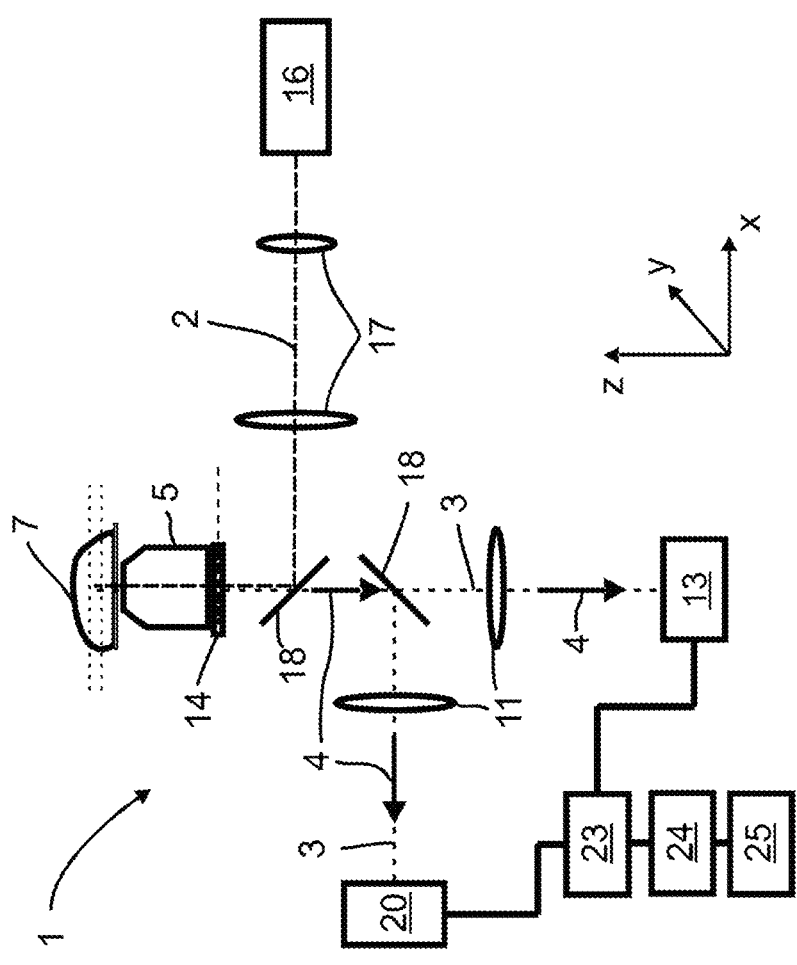
FIG. 3 shows a schematic illustration of a second exemplary embodiment of an apparatus.

A first exemplary implementation of an apparatus is shown in FIG. 3 as part of a microscope 1 not illustrated in any more detail. Illumination radiation is generated and provided in a laser light source 16. The illumination beam reaches the objective 5 via a beam splitter 18 in reflection along the illumination beam path 2, in which optical lenses 17 are situated. An optical element 14 in the form of a phase element is arranged in or in the vicinity of a Fourier plane of the objective 5. In a Fourier plane, a point is transformed into a plane wave and, conversely, a plane wave is transformed into a point. So that the respectively present phase element has the same action on all object points, it should be located in the Fourier plane or be arranged as close as possible to a Fourier plane.

An extended depth of field EDOF of the objective 5 is achieved by the action of the optical element 14. In the sample 7, the illumination radiation causes detection radiation 4, which strikes the beam splitter 18 along the detection beam path 3. The detection radiation 4 deviates from the illumination radiation in terms of its optical properties and is transmitted by the beam splitter 18. If the detection radiation 4 is formed by radiation of at least two wavelengths, these can be separated from one another and can be captured separately. In the illustrated exemplary embodiment, such a separation is brought about by means of a further beam splitter 18, which is transparent to one wavelength and reflective for another wavelength. Detection radiation 4 split in this way reaches the detector 13 or a further detector 20 along partial beam paths.

The detectors 13 and 20 are connected to an evaluation unit 23, by means of which the captured signals 12 are processed as image data and evaluated. Moreover, a control unit 24 is present, by means of which the control commands for controlling, e.g., the laser light source 16, the optical element 14, the tube lens 11, and/or the optical lenses 17 can be generated and output. The image data and information regarding generated control commands and/or the current configuration of the apparatus can be displayed on a display 25.

Figure 4:
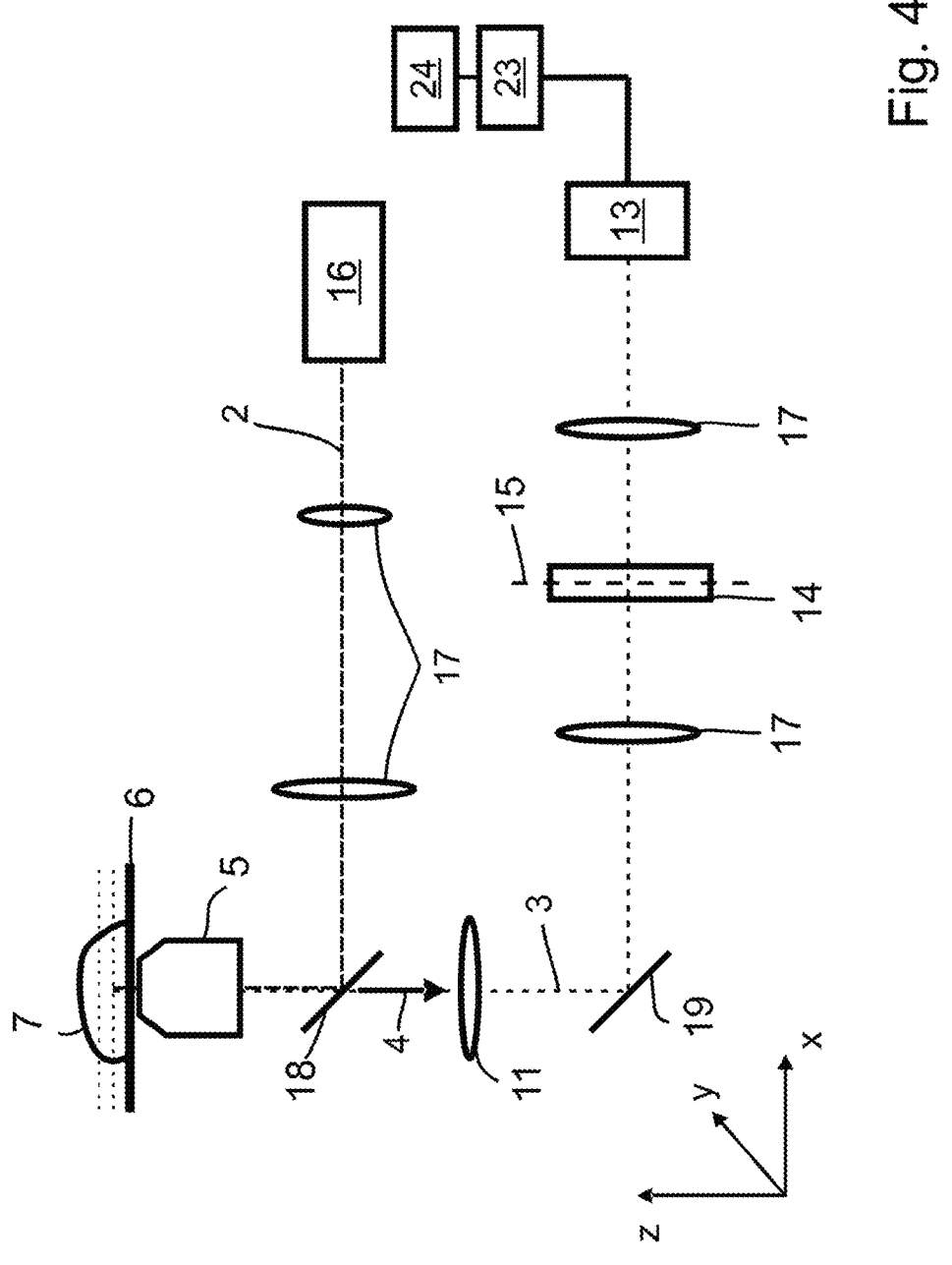
FIG. 4 shows a schematic illustration of a third exemplary embodiment of an apparatus.

The arrangement of the optical element 14 in a pupil-conjugate plane (Fourier plane) (FIG. 4) can be chosen so that the illumination radiation does not pass through the optical element 14. In the illustrated third exemplary embodiment, illumination beam path 2 and detection beam path 3, or the illumination radiation and the detection radiation 4, are split from one another by means of a beam splitter 18. The detection radiation 4 is steered to the optical element 14 and the detector 13 by means of a mirror 19.

Figure 5:
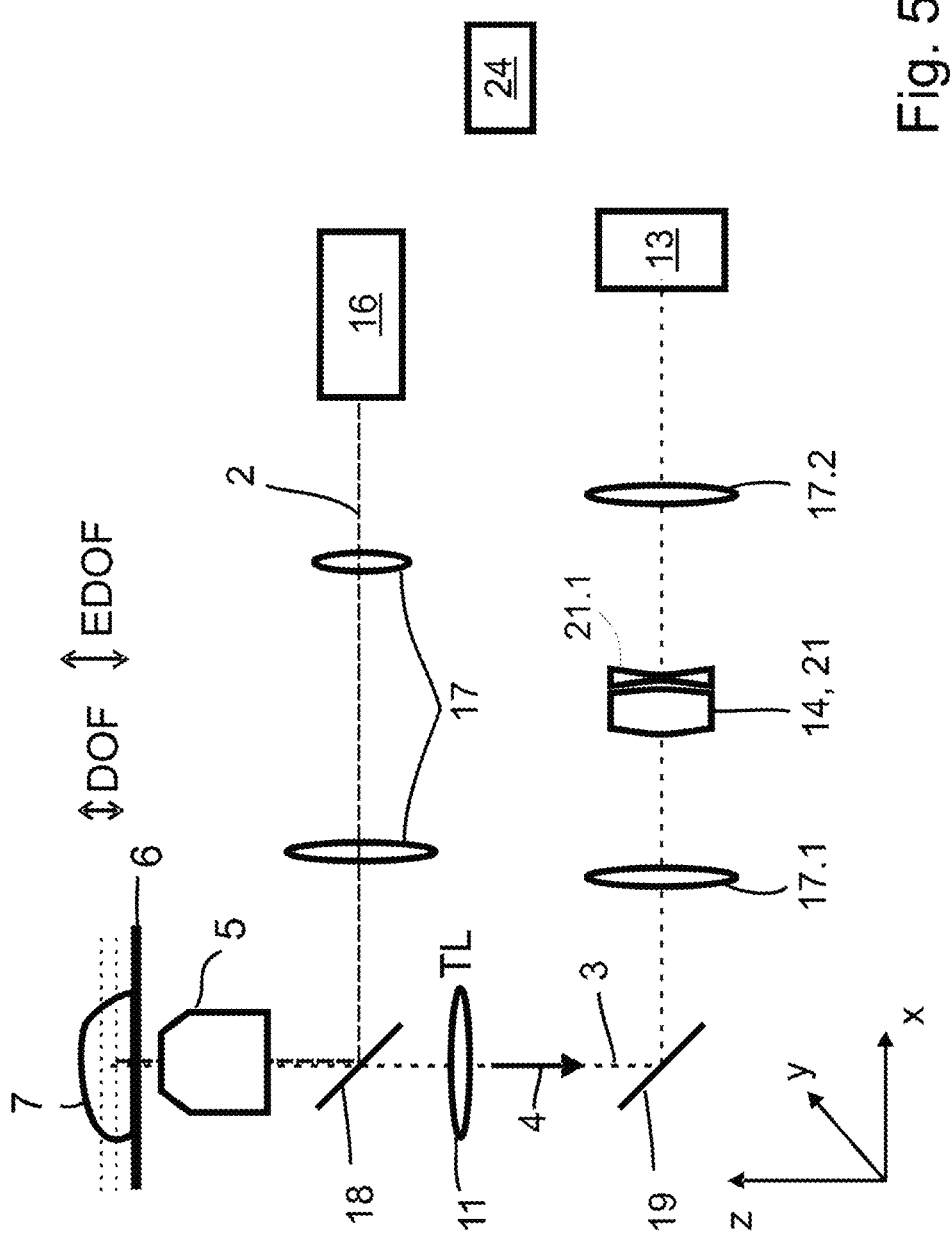
FIG. 5 shows a schematic illustration of a fourth exemplary embodiment of an apparatus.

A further possible exemplary embodiment of an apparatus (FIG. 5) is suitable for attaining an extended depth of field EDOF by means of a fast displacement of the respective focal plane DOF. An intermediate image downstream of the tube lens 11 is imaged on the detector 13 by means of two lenses 17.1 and 17.2 illustrated in exemplary fashion in the detection beam path 3. Below, the lenses 17.1 and 17.2 can also represent more complex imaging optical units. A varifocal lens 21, which facilitates a displacement of the current focal plane DOF and the generation of an extended depth of field EDOF, is present between the lenses 17.1 and 17.2. The varifocal lens 21 can additionally include a compensation lens 21.1, as shown schematically in FIG. 5. The varifocal lens 21 is controllable by means of the control unit 24. In particular, control can be implemented so quickly that at least two current focal planes DOF are set within a capture time interval of the detector 13 and consequently a resultant extended depth of field EDOF is generated. The detection radiation 4 is captured with the (resultant) extended depth of field EDOF.

Figure 6:
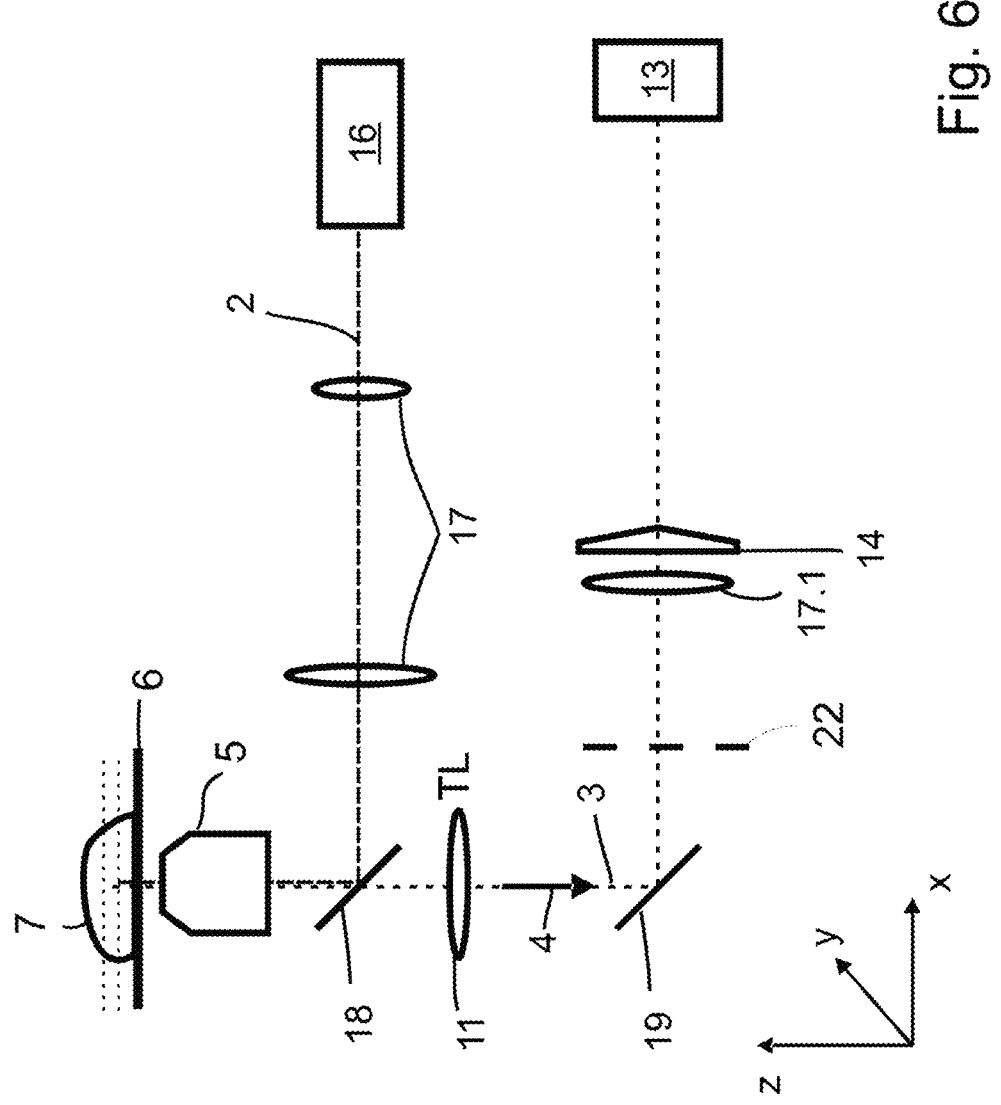
FIG. 6 shows a schematic illustration of a fifth exemplary embodiment of an apparatus.

An axicon is arranged in the detection beam path 3 as an optical element 14 in a further exemplary implementation of the apparatus (FIG. 6). The optical element 14 is arranged in the vicinity of the lens 17.1, the latter in turn being arranged at a distance from an intermediate image plane 22 in accordance with its focal length.

Figure 7:
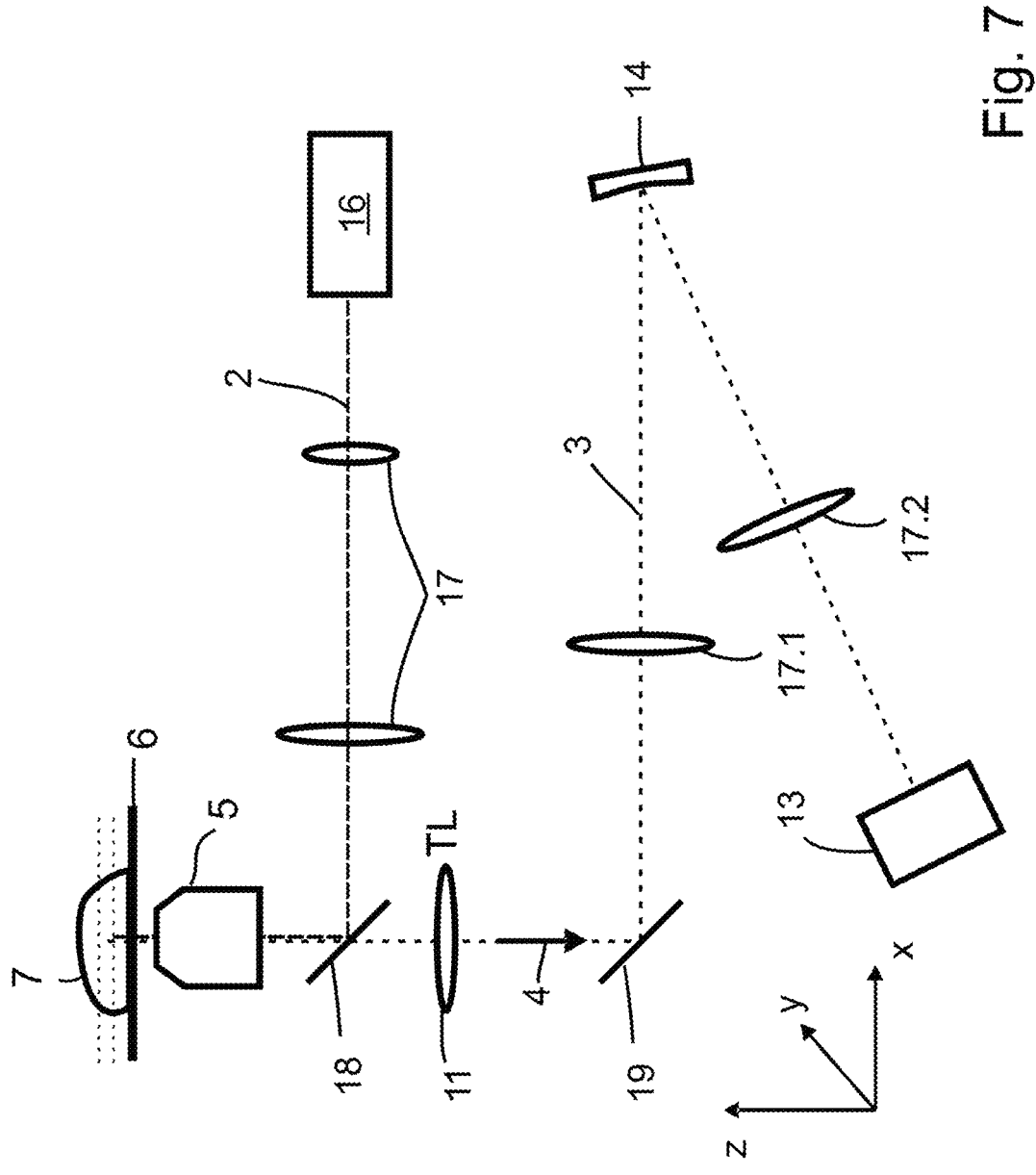
FIG. 7 shows a schematic illustration of a sixth exemplary embodiment of an apparatus.

A further implementation option of the apparatus can facilitate a dynamic generation of the extended depth of field EDOF using an adaptive mirror or a microlens array as an optical element 14 (FIG. 7). The lenses 17.1 and 17.2 in the detection beam path 3 image a first intermediate image on the detector 13. The optical element 14 is present in a pupil 15 (pupil plane).

Figure 8:
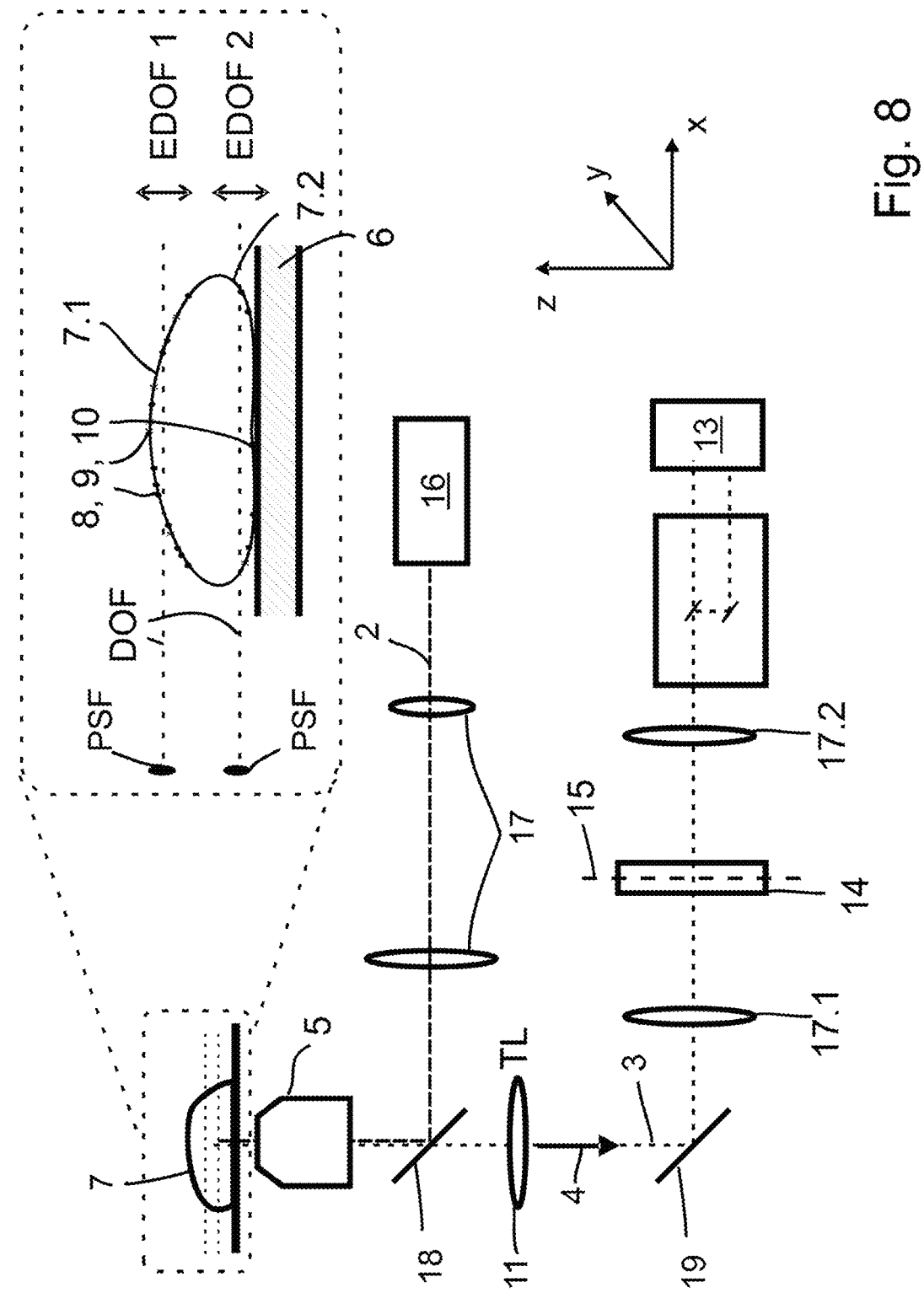
FIG. 8 shows a schematic illustration of a seventh exemplary embodiment of an apparatus.

One exemplary embodiment for multifocal imaging combined with an extended depth of field EDOF is elucidated in FIG. 8. The lenses 17.1 and 17.2 image the intermediate image on the detector 13 and simultaneously create a further conjugate pupil 15. The optical element 14 is arranged in the latter. The lenses 17.1 and 17.2 provide a so-called relay optical unit.

The detection radiation 4 is captured with a respective depth of field DOF with a plurality of mutually different focal planes, wherein the effect of the optical element 14 generates an extended depth of field EDOF1 or EDOF2 around each of the focal planes, as shown schematically in the magnified partial illustration. In this case, the extended depth of field EDOF1 allows imaging of signals 12 of markers 8, antigens 9 connected to marked antibodies 10, and/or marked antibodies 10 of the upper cell membrane 7.1 and the extended depth of field EDOF2 allows imaging of signals 12 of markers 8, antigens 9 connected to marked antibodies 10, and/or marked antibodies 10 of the lower cell membrane 7.2.

In further embodiments of the apparatus and/or configurations of the method, the depths of field DOF or the extended depths of field EDOF advantageously slightly overlap in the direction of the z-axis Z in order to allow interruption-free imaging of the relevant sample volume.

Furthermore, an image splitter unit 26 is arranged in the detection beam path 3. By means of the latter, the components of the detection radiation 4 from the different focal planes DOF or the different extended depths of field EDOF1, EDOF2 are directed at different detectors 13 or at different regions of at least one detector 13 and are captured separately from one another.

Figures 9A, 9B, 9C:
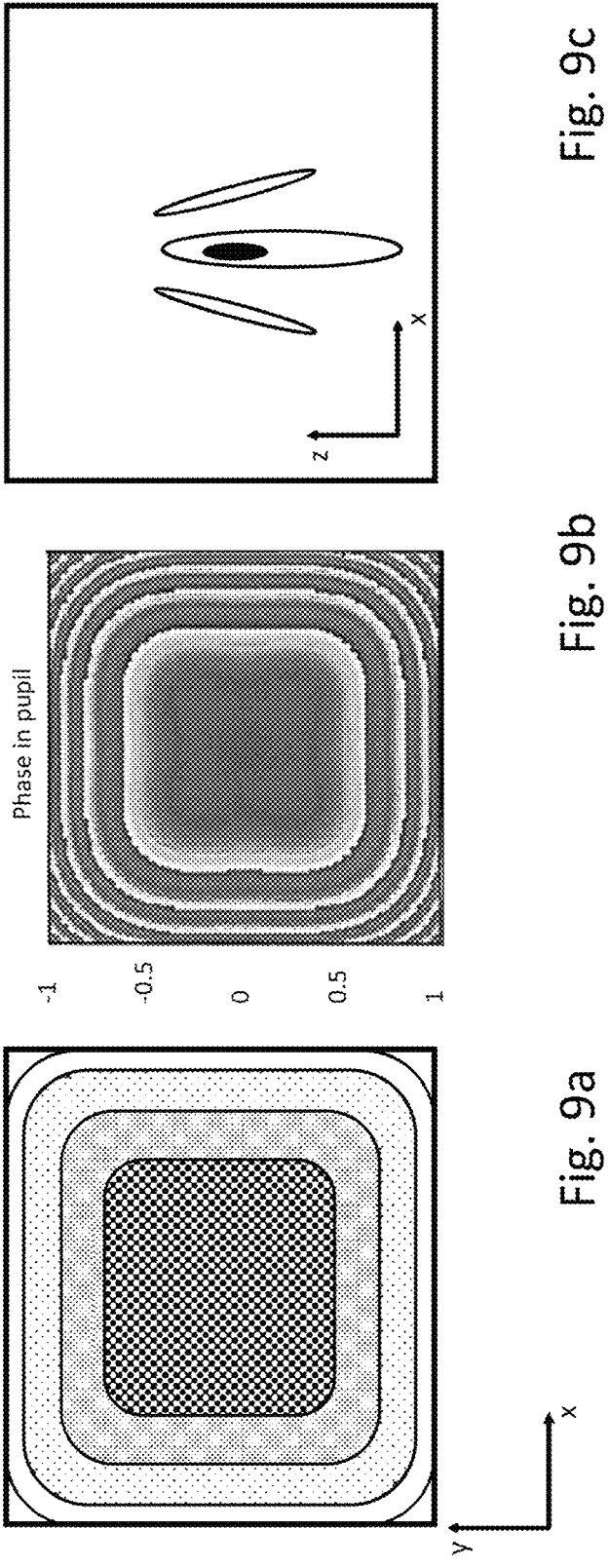
FIG. 9 shows a schematic illustration of a phase distribution in a pupil of a detection beam path by the effect of a symmetric cubic phase mask, respectively as a) a simplified black-and-white sketch, b) as a grayscale image, and c) a simplified illustration of the associated point spread function.
Figures 10A, 10B, 10C:
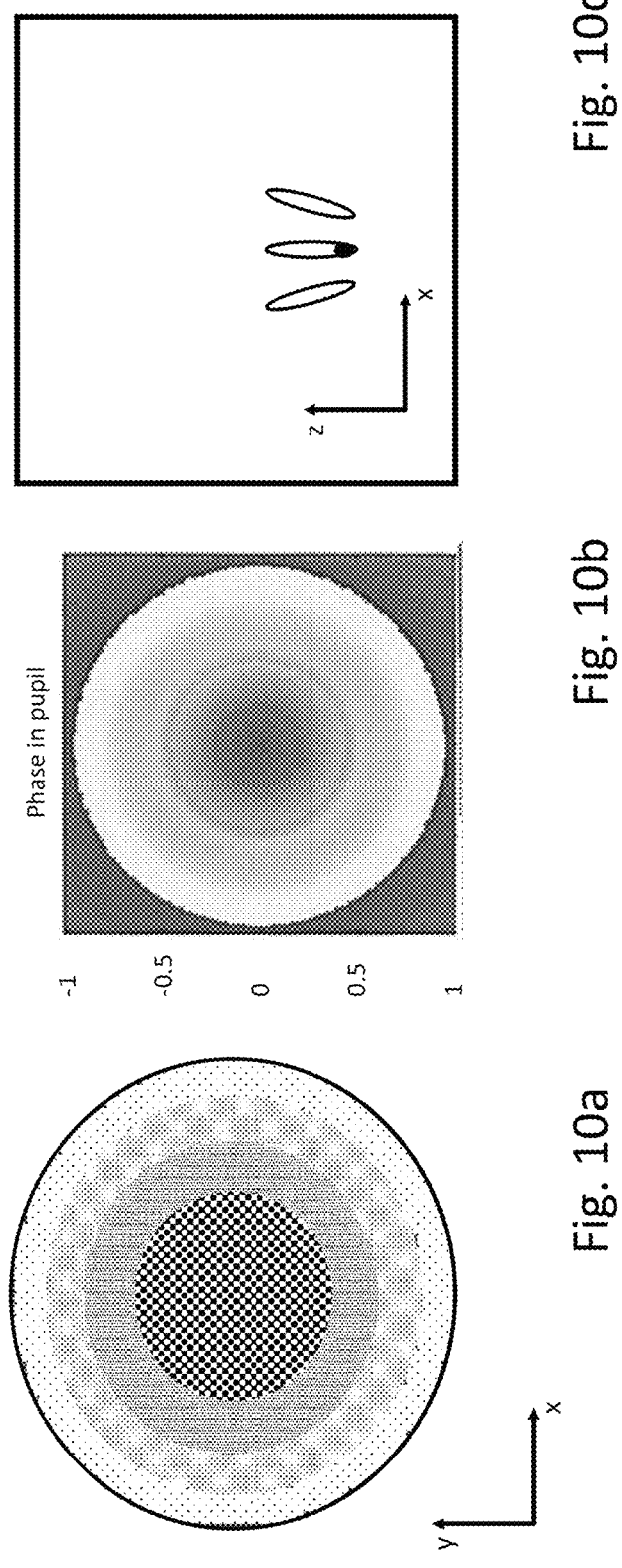
FIG. 10 shows a schematic illustration of a phase distribution in a pupil of a detection beam path by the effect of an axicon, respectively as a) a simplified black-and-white sketch, b) as a grayscale image, and c) a simplified illustration of the associated point spread function.
Figures 11A, 11B, 11C:
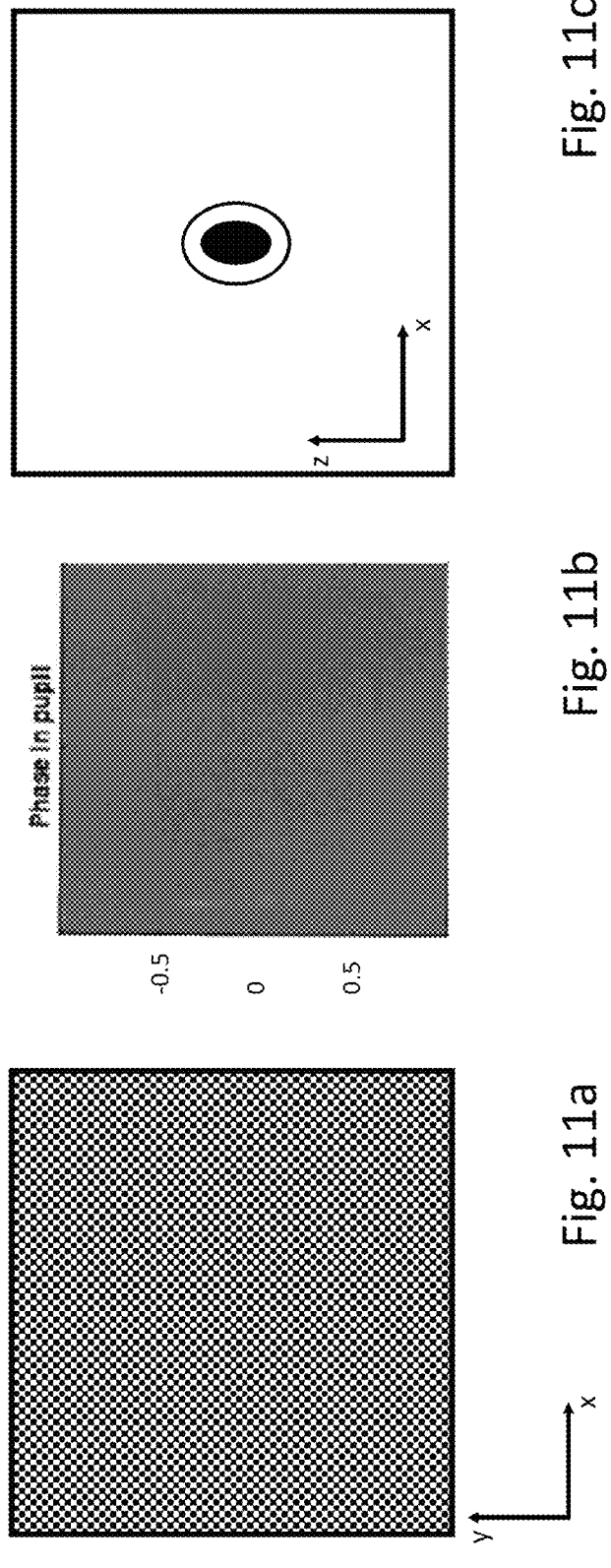
FIG. 11 shows a schematic illustration of a phase distribution in a pupil of a detection beam path without the effect of an optical element, as a) a simplified black-and-white sketch, b) as a grayscale image, and c) a simplified illustration of the associated point spread function.

An extended depth of field EDOF can be generated using phase masks. Phase distributions in a pupil of a detection beam path as a result of the effect of different phase masks are shown in FIG. 9 to FIG. 11. In this case, partial FIGS. 9*a*, 10*a*, and 11*a* each show a simplified black-and-white sketch of the grayscale images illustrated in FIGS. 9*b*, 10*b*, and 11*b* with corresponding phase distributions in an xy-plane. FIGS. 9c, 10c, and 11c, respectively, illustrate the simplified point spread functions PSF as a section in an xz-plane in each case.

FIGS. 9a to 9c show the sketch, the grayscale image, and the PSF of a symmetric cubic phase mask.

FIGS. 10a to 10c show the corresponding phase distributions and the PSF of an axicon.

Phase distribution and PSF without the arrangement of an optical element 14 in the detection beam path 3 are illustrated in exemplary fashion in FIGS. 11a to 11c.

Figure 12B:
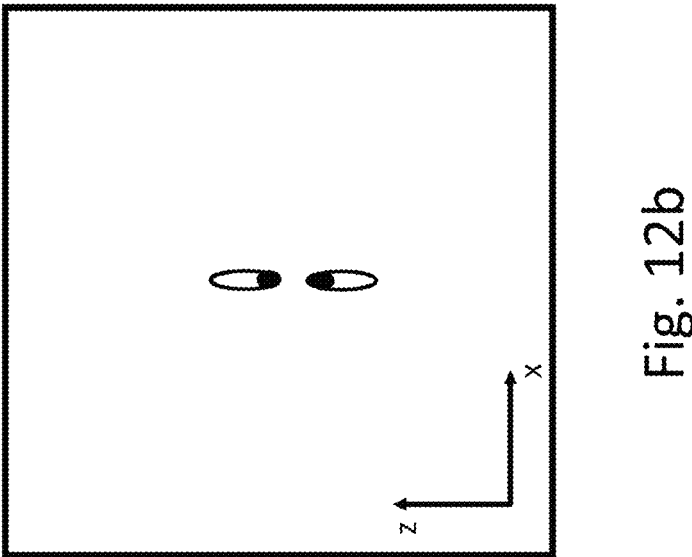
FIG. 12 shows a schematic illustration of a) a phase distribution of a first ring phase mask in a pupil plane of a detection beam path and b) a much-simplified illustration of an associated simulated point spread function.
Figure 12A:
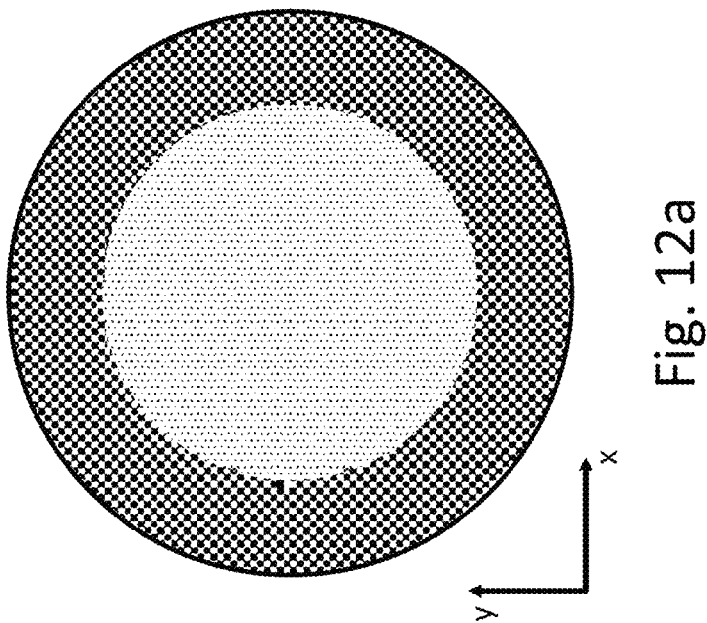
Figure 13B:
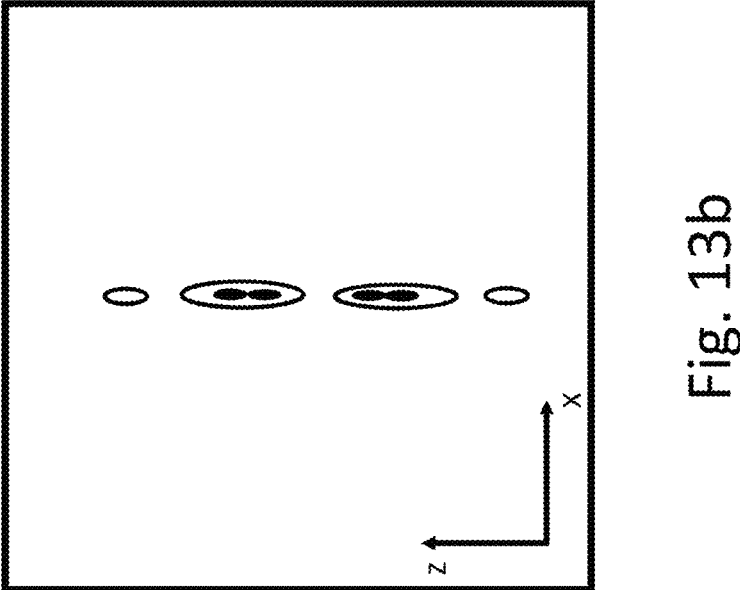
FIG. 13 shows a schematic illustration of a) a phase distribution of a second ring phase mask in a pupil plane of a detection beam path and b) a much-simplified illustration of an associated simulated point spread function.
Figure 13A:
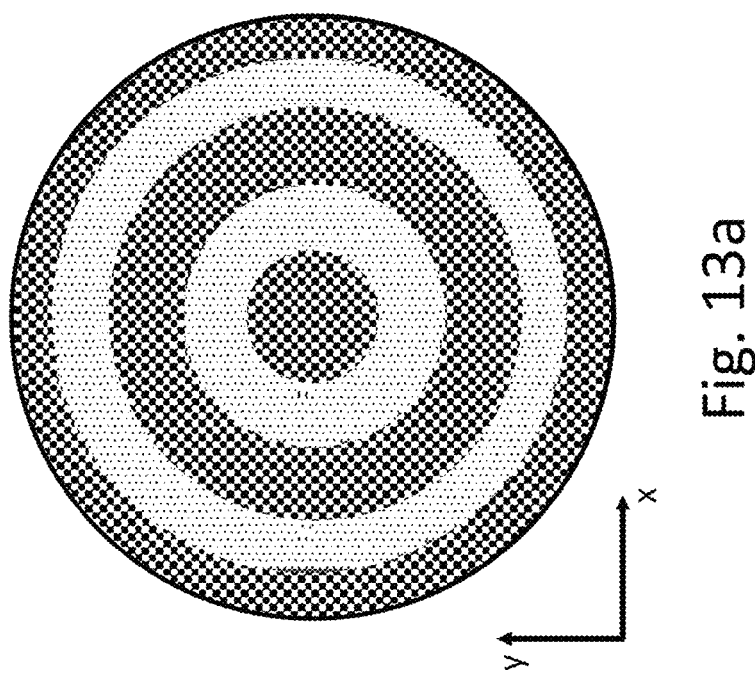
Figure 14B:
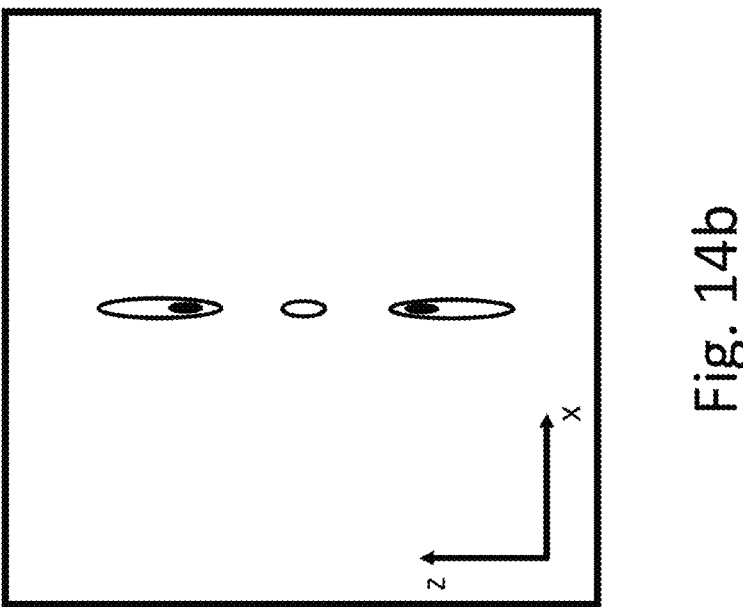
FIG. 14 shows a schematic illustration of a) a phase distribution of a third ring phase mask in a pupil plane of a detection beam path and b) a much-simplified illustration of an associated simulated point spread function.
Figure 14A:
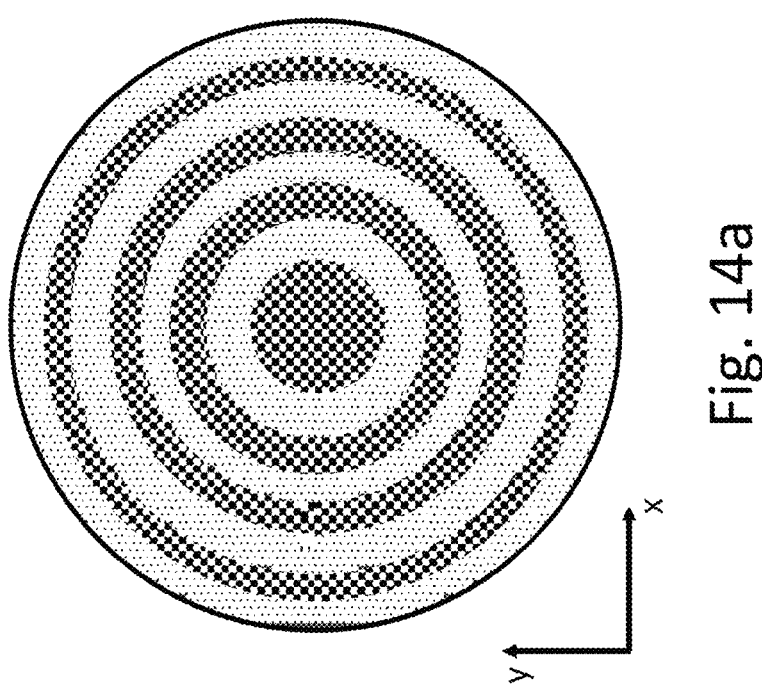

Various ring phase masks and their respective simulated point spread functions are shown in FIGS. 12 to 14. In this case, FIGS. 12a, 13a, and 14a each schematically show a generated ring phase mask. FIGS. 12b to 14b illustrate the associated point spread functions PSF in simplified fashion.

FIG. 12 relates to a ring phase mask with a phase shift of π between the differently hatched regions. The resultant PSF shows two separate maxima in the direction of the Z-axis Z.

A ring phase mask with a plurality of different regions, once again with a phase shift of π in each case, is illustrated schematically in FIG. 13a. The associated point spread function PSF is pulled apart in the direction of the Z-axis Z. At least two separate maxima occur, with these having a clearly identifiable tendency of forming further maxima. Ring phase masks with more than the shown regions and phase shifts allow additional maxima and hence focal planes DOF and/or extended depths of field EDOF. Depending on the design of the phase masks, the point spread function PSF can be matched to the sample 7 to be imaged and/or to the sought-after object of the imaging.

Figure 15:
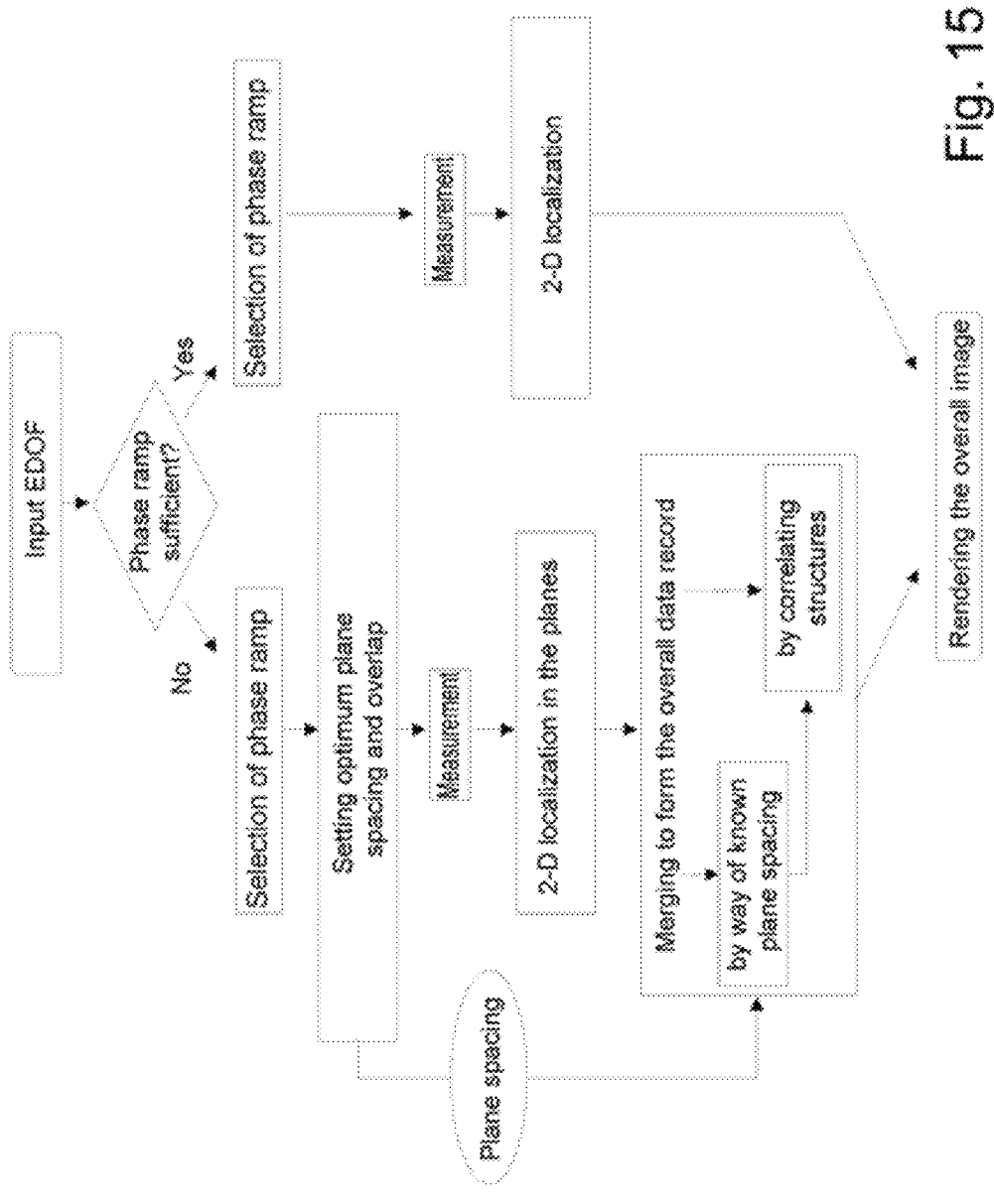
FIG. 15 shows a flowchart of a configuration of a method.

Configuration options of the method are explained on the basis of the flowchart in FIG. 15. In particular, one of the above-described embodiment options of the apparatus is used to carry out the method.

A sample 7 that is expected to potentially emit fluorescence signals or light-induced light signals is provided. By way of example, such samples 7 are biological surfaces with at least one antibody 10, which is compatible with an antigen 9 to be detected and which is provided with a marker 8 suitable for emitting light signals. However, a biological surface incubated with such an antibody 10 can also be used as a sample 7.

An extended depth of field EDOF is chosen, by means of which the relevant sample 7 should be examined for the presence of fluorescence signals 12. If a current setting or configuration of the apparatus, for example, a currently set phase ramp, allows the detection of the signals 12 with the desired extended depth of field EDOF, the measurements are carried out with this configuration. To this end, the sample 7 is illuminated with the illumination radiation, the latter facilitating and/or potentially triggering the emission of the signals 12. If the illumination radiation acts as excitation radiation, markers 8 which are present in the illuminated region of the sample 7 and which are receptive to the illumination radiation are excited to emit signals 12.

The emitted signals 12 are imaged by means of the apparatus and the currently set extended depth of field EDOF on the at least one detector 13, 20 arranged in the detection beam path 3 and are captured by said detector as image data (measurement). The spatial resolution of the detector 13, 20 facilitates a two-dimensional assignment (2-D localization) of the location of origin of the respective signal 12 in an XY-plane. A localization in the direction of the Z-axis Z is possible, at best, to the effect of the origin of the signal 12 being known as coming from the region of the extended depth of field EDOF and so a correspondingly coarse region in the direction of the Z-axis Z being able to be assigned to a position in the XY-plane. The localization assists the check for possible two-time capture of signals 12 and a possibly required correction of the detection and/or count results of the method.

The captured image data are merged to form a resultant overall image, for example, by means of the evaluation unit 23; this is also referred to as image synthesis or rendering.

In an alternative course of the method, it is determined that the chosen extended depth of field EDOF cannot be attained with the current configuration of the apparatus, in particular with the current phase ramp. In the illustrated example, the extended depth of field EDOF should be generated by a plurality of focal planes DOF, which are located sufficiently close to one another in the direction of the Z-axis Z.

Therefore, the optimum spacings of the focal planes DOF and the overlap thereof are set for the desired extended depth of field EDOF. By means of the apparatus set thus, the measurement and the localization of the respectively captured signal 12 is implemented in the respective focal planes DOF and/or in the region of the extended depth of field EDOF.

The captured image data of the individual focal planes DOF, and hence of the extended depth of field EDOF, are subsequently combined to form an overall data record. In the process, it is possible to use the known spacings and/or overlaps of the focal planes DOF. In addition, or as an alternative thereto, structures of the sample 7, which are contained in the image data and which have been identified, can be used to verify ascertained localization data by way of correlations of the structure data. The overall data record obtained thus, which may have been verified where necessary, is merged to form a resultant overall image.

Additionally, a value of the plane spacing can be provided and can be included in the combination method step to form an overall data record. By way of example, this optional value is advantageous if a plurality of objects, e.g., cells, are present above one another or if image data are captured in tissues.

REFERENCE SIGNS

1 Microscope
2 Illumination beam path
3 Detection beam path
4 Detection radiation
5 Objective
6 Slide
7 Sample
7.1 Lower cell membrane
7.2 Upper cell membrane
8 Marker
9 Antigen
10 Antibody
DOF Focal plane; original depth of field
EDOF Focal region; extended depth of field
PSF Point spread function
11 Tube lens
12 Fluorescence signal
13 Detector
14 Optical element
15 Pupil
16 Laser light source
17 Lens
17.1 Lens
17.2 Lens
18 Beam splitter

19 Mirror
20 Further detector
21 Varifocal lens
21.1 Compensation lens
22 Intermediate image plane
23 Evaluation unit
24 Control unit
25 Display
26 Image splitter unit

The invention claimed is:

1. A method of detecting optical signals in a three-dimensional region of a sample, the method comprising:

capturing image data of the three-dimensional region as two-dimensionally super-resolved image data by means of an optical apparatus in a two-dimensional image plane, wherein the super-resolved image data includes fluorescence signals from individual photoswitchable marker molecules that are located relative to one another by distances below a resolution limit of the optical apparatus, wherein capturing the image data includes capturing signals as of fluorescence signals from different subsets of photoswitchable marker molecules with a depth of field that is extended in relation to an original depth of field of the apparatus and are projected into an image plane, wherein the signals from the different subsets are captured in a time series;

evaluating the captured image data to ascertain a number of the captured signals, wherein evaluating the image data read from the optical apparatus to ascertain the number of the captured signals includes ascertaining a number of the captured signals emitted from individual photoswitchable marker molecules from each subset of the time series, and determining the number based on the numbers of captured signals captured from each subset of the time series; and storing the number in a manner assigned to the image region and providing the assigned number.

2. The method as claimed in claim 1, further comprising generating at least two focal planes with an original depth of field or at least two focal regions with an extended depth of field or at least one focal plane with an original depth of field and at least one focal region with an extended depth of field to generate the extended depth of field.

3. A method of detecting an antigen on a biological surface which is incubated with at least one antibody that is compatible with the antigen and which is provided with photoswitchable marker molecules suitable for induced emission of signals as fluorescence signals and/or induced light signals, the method comprising:

exciting different subsets of the photoswitchable marker molecules associated with the at least one antibody marked by the photoswitchable marker molecules and bound to the antigen in each case to emit signals;

guiding detection radiation corresponding to the signals emitted from the excited marked at least one antibody along a detection beam path, imaging the detection radiation with an objective having an original depth of field in a direction of a detection axis in the detection beam path onto a detector, wherein the detector is configured for two-dimensionally resolved capture of the detection radiation and wherein the detection radiation corresponding to the signals from the different subsets are imaged in a time series;

extending the original depth of field with an optical element located in a pupil of the detection beam path;

evaluating image data read from the detector, the image data corresponding to two-dimensionally super-resolved detection radiation captured with the extended depth of field of the objective, wherein the super-resolved detection radiation includes fluorescence signals from individual photoswitchable marker molecules that are located relative to one another by distances below a resolution limit of the objective, to ascertain a number of the captured signals, wherein evaluating the image data read from the detector to ascertain the number of the captured signals emitted from the excited marked antibodies includes ascertaining a number of the captured signals emitted from the excited marked antibodies captured from each subset of the time series, and determining the number based on the numbers of captured signals captured from each subset of the time series; and storing and providing the number of the captured signals.

4. The method as claimed in claim 3, wherein extending the original depth of filed includes generating at least two focal planes with an original depth of field or at least two focal regions with an extended depth of field or at least one focal plane with an original depth of field and at least one focal region with an extended depth of field.

5. The method of claim 3, further comprising:

incubating the biological surface with the at least one antibody which is compatible with the antigen to be detected and which is provided with a marker suitable for the induced emission of signals as fluorescence signals and/or induced light signals.

6. An apparatus for detecting fluorescence signals and/or induced light signals emitted from a three-dimensional region of a sample, the apparatus comprising:

a detection beam path configured for guiding detection radiation corresponding to the signals emitted from different subsets of photoswitchable marker molecules in the three- dimensional region of the sample;

a detection objective having an original depth of field in a direction of a detection axis in the detection beam path and configured for imaging the detection radiation;

an optical element located in a pupil of the detection beam path, the optical element being configured to extend the depth of field over the original depth of field;

a detector configured to capture from the detection radiation guided along the detection beam path, and to resolve in two-dimensions, the signals as image data, wherein the detection objective is configured to image the detection radiation onto the detector; and a computer configured to:

cause the signals emitted from the different subsets of photoswitchable marker molecules to be captured by the detector in a time series;

process the image data to generate two-dimensionally super-resolved image data, wherein the super-resolved image data includes fluorescence signals from individual photoswitchable marker molecules of the subsets of photoswitchable marker molecules, which are located relative to one another by distances below a resolution limit of the optical apparatus, and evaluate the image data read from the detector, based on a point spread function (PSF) of the detection objective, which is modified along the detection beam path by the depth of field that is extended over the original depth of field, to ascertain a number of the captured signals, to assign the number of signals to an image region, and to store the number of signals assigned to the image region, wherein evaluating the image data read from the optical apparatus to ascertain the number of the captured signals includes ascertaining a number of the captured sig-
nals emitted from individual photoswitchable marker
molecules from each subset of the time series, and
determine the number based on the numbers of cap-
tured signals captured from each subset of the time
series.

7. The apparatus as claimed in claim 6, wherein the
optical element includes an axicon or an axicon phase mask
configured to convert the detection radiation into a Bessel
beam.

8. The apparatus as claimed in claim 6, wherein the
optical element includes a cubic phase mask.

9. The apparatus as claimed in claim 6, wherein the
optical element includes a ring phase mask.

10. The apparatus as claimed in claim 6, wherein the
optical element includes a birefringent element.

11. The apparatus as claimed in claim 6, wherein the
optical element includes at least one liquid lens, an adaptive
mirror, or a microlens array.

12. The apparatus as claimed in claim 6, further compris-
ing:
   a laser light source configured for providing illumination
      radiation; and
   an illumination objective configured for receiving the
      illumination radiation and generating a light sheet in
      the sample, the light sheet having a thickness corre-
      sponding to an extended depth of field region.

13. The apparatus as claimed in claim 12, wherein the
illumination objective and the detection objective are the
same objective.

* * * * *

18